United States Patent [19]

Ruddle

[11] Patent Number: 5,797,745
[45] Date of Patent: Aug. 25, 1998

[54] RADIOPAQUE SOLUTION FOR VISUALIZING DENTAL ANATOMY, PATHOLOGICAL CONDITIONS, AND IATROGENIC EVENTS, AND METHOD OF USE

[76] Inventor: Clifford J. Ruddle, 227 Las Alturas Rd., Santa Barbara, Calif. 93103

[21] Appl. No.: 770,287

[22] Filed: Dec. 20, 1996

[51] Int. Cl.$^6$ ................................................ A61C 5/10
[52] U.S. Cl. .......................... 433/224; 433/81; 424/51
[58] Field of Search ........................ 433/224, 81, 215, 433/86; 423/117; 424/51

[56] References Cited

U.S. PATENT DOCUMENTS

| | | | |
|---|---|---|---|
| 5,106,301 | 4/1992 | Miyahara et al. | 433/214 |
| 5,318,788 | 6/1994 | Illig et al. | 424/5 |

OTHER PUBLICATIONS

Scarfe, et al., Journal of Endodontics, Apr. 1995, vol. 21, No. 4, pp. 185–190.
Shearer, et al., International Endodontic Journal, 1996, vol. 29, pp. 95–98.

*Primary Examiner*—Cary E. O'Connor
*Attorney, Agent, or Firm*—Polster, Lieder, Woodruff & Lucchesi

[57] ABSTRACT

A radiopaque composition for use in visualizing and cleaning root canal system anatomy, pathologies, anomalies, and iatrogenic conditions. The composition comprises a radiopaque iodine solution and a sodium hypochlorite solution. The iodine solution comprises diatrizoate meglumine and sodium iodine. The iodine solution and sodium hypochlorite solution are mixed in a ratio of between 5:95 to 95:5, by volume. Preferably, the iodine solution and sodium hypochlorite solution are mixed in a ratio of between 30:70 to 70:30, by volume. And more preferably, the iodine solution and sodium hypochlorite solution are mixed in a ratio of between 45:55 to 55:45, by volume. In use, the root canal system anatomy, anomaly, pathology, or iatrogenic condition to be visualized and addressed or treated is liberally flushed with the composition, preferably after the root canal system has been exposed. The sodium hypochlorite in the composition will digest pulp in the canal system and destroy and remove any organisms and irritants residing in or on the anatomy, anomaly, or pathology. The iodine in the solution will enable a dentist to take a high contrast X-ray to visualize the anatomy, anomaly, pathology, or iatrogenic event in three-dimensions. The solution is particularly effective for visualizing root canal systems.

24 Claims, No Drawings

RADIOPAQUE SOLUTION FOR VISUALIZING DENTAL ANATOMY, PATHOLOGICAL CONDITIONS, AND IATROGENIC EVENTS, AND METHOD OF USE

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

This invention relates to a radiopaque solution for use in visualizing root canal system anatomy, pathological conditions, and iatrogenic events. In particular, the invention relates to a radiopaque solution that will encourage cleaning and shaping of the root canal systems for obturations and simultaneously enhance radiographic interpretation of root canal system anatomy and structure. It can also be used to assist in the diagnosis and extent of fractures, distinguish between internal and external resorptions, map the size and extent of repsorptive pathologies, visualize blocked and ledged canals, verify the shape and remaining wall thickness during root canal preparation, and other diagnostic possibilities, including visualizing iatrogenic occurrences.

Following tooth maturation, the dental pulp is harbored within the structural elements of the tooth. Frequently, and for a variety of reasons, the pulp is irreversibly injured, resulting in inflammatory and infectious conditions which often adversely affect tooth structures and/or the supporting tissues. Clinically, as an alternative to extraction, root canal treatment is performed and ideally directed towards the elimination of pulp, bacteria and irritants from the root canal system, followed by filling the canal space with an inert, biocompatible, dimensionally stable, three-dimensional root canal filling material. That is, the complete root canal system, not just the trunk of the root canal, is filled with the material.

Many factors influence successful endodontic treatment and retreatment when necessary. Such factors include diagnosis, complete access to and identification of all the orifices, and threedimensionally cleaning, shaping, and packing the root canal system. Other critical factors contributing to a successful retention of teeth are calcifications, identification of all orifices/systems, canal anatomy, resorptions, previous treatment complexities, materials, iatrogenic events, periodontal potential, fractures, restorative competence, doctor ability and experience, patient cooperation, time, cost, alternatives, and other variables.

Root canal procedures are common. In 1994 alone, some 40 million root canal procedures were performed in the United States. Central to a successful endodontic treatment has been the use of chemicals to enhance canal debridement during cleaning and shaping procedures to facilitate the preparation and complete cleaning of the root canal system. Root canal systems are often complex in structure. They can include fins, lateral canals, dentinal tubules, and accessory root canals. The complex structure of the root canal system makes it difficult to remove the pulp from the root canal using only mechanical instruments. The chemicals chosen to facilitate preparation and cleaning root canal systems are selected to destroy organisms and irritants, digest tissue, and promote cleaning and shaping procedures while encouraging aesthetics. The chemicals used to enhance canal debridement during cleaning and shaping procedures reach all aspects of the root canal system. The most popular chemicals currently used during canal preparation to actively assist in cleaning include bleach, hydrogen peroxide, and chelating agents. Often, a 1.5%–5% solution of a clear, pale, greenish-yellow strongly alkaline solution of sodium hypochlorite (NaOCl) is used.

During canal preparation, the sodium hypochlorite solution is liberally irrigated into the root canal space where its solvent action facilitates the digestion and removal of pulp and bacteria and the destruction and removal of viruses, spores, endotoxins and other irritants generated by the microorganisms in the canal system as the solution penetrates into all aspects of the root canal system. Such solutions, however, do not aid the dentist in determining the anatomy of the root canal system or other anomalies or pathologies of a patient's tooth. "Dentist" is used broadly herein to include all those who perform dental work, and is intended to include, for example, general dentists and specialists within the fields of dentistry, such as oral surgery, endodontics, pedodontics, etc.

To completely fill or pack root canal systems it would be highly advantageous to know with a high degree of certainty the exact configuration of the root canal systems prior to obturation. The above noted complexities are impossible to visualize with the sodium hypochlorite solution alone. Mechanical exploration of the tooth with dental instruments has been used to determine the configuration of the root canal system. However, during instrumentation, it is difficult, if not impossible, to completely understand the complete anatomy of the root canal system. X-rays have been used in an attempt to visualize the canal system. However, even conventional, well angulated X-rays of the tooth only show resolutions to about 50 microns. This degree of resolution is insufficient to reveal the complete anatomy and structure of the root canal systems.

Currently, endodontic treatment, retreatment, or interim treatment is evaluated after the fact based on metals, cements, or other solid materials that "show up" radiopaque or white on a radiograph or X-ray. Examples of such items are files, instruments, burs, interim medicaments and definitive filling and restorative materials. Experimentally, certain researchers have turned to the use of impression materials to form an actual mold of the root canal system. One such method is shown, for example, in U.S. Pat. No. 5,106,301 to Miyahara et al. However, the use of such a method requires that the mold material be poured into the root canal system, allowed to set, and then extracted from the root canal system so that the configuration can be seen in three dimensions. However, as root canal systems are highly complex, removal of the mold from the tooth is difficult, and frequently portions of the molding material are left in the tooth. In fact, Miyahara et al. dissolved the tooth to see the molded root canal system. This method will not give the dentist the configuration of the root canal system and, if the dentist were to use this on an actual patient, he would be posed with the impossible challenge of removing the retained molding material from the tooth prior to completing a conventional endodontics. This obviously adds time and frustration to the procedure and lowers the prognosis because conventional irrigants and digestants cannot digest or remove the molding material.

Except for a few published research studies, all of which are believed to be in vitro, dentistry has never routinely used radiopaque solutions to visualize a patient's root canal system anatomy, let alone, a variety of pathological or iatrogenic conditions. In contrast, medicine has clinically used a high contrast injectable dye, such as Hypaque®, available from Sterling-Winthrop, Inc., of New York, N.Y., for angiography, arteriography, urography, and nephrotomography. Hypaque-M is a high concentration, highly viscous, aqueous solution of two iodine salts, diatrizoate meglumine and sodium iodine, has a pH of between 6.7–7.7, and is stable at room temperature.

In addition to visualizing root canal anatomy, a radiopaque solution could assist in the diagnosis and extent of fractures, distinguish between internal and external resorptions, map the size and extent of resorptive pathologies, track decay, confirm leaking restorations, identify the size and position of perforations, visualize blocked and ledged canals, verify the shape and remaining wall thickness during canal preparation, and can assist in other diagnostic possibilities. In some of the above mentioned pathologies, it would enable the dentist to determine the best course of action to take to salvage the tooth.

BRIEF SUMMARY OF THE INVENTION

One object of the present invention is to provide a radiopaque solution for visualizing dental anatomy, pathology, and iatrogenic events.

Another object is to provide such a solution for visualizing the root canal systems of a tooth.

Another object is to provide such a solution which can be used to confirm the cleaning and shaping procedures during a root canal procedure.

Another object is to provide such a solution which can be used to visualize the size and extent of the canal preparation of a tooth and to confirm the amount of remaining wall thickness during canal preparation.

Another object is to provide a solution for use in assisting in the diagnosis and extent of fractures, distinguishing between internal and external resorptions, mapping the size and extent of resorptive pathologies, tracking decay, and confirming leaking restorations.

Another object is to provide such a solution which can be used to visualize iatrogenic events, such as blocked and ledged canals and the size and position of perforations.

These and other objects will become apparent to those skilled in the art in light of the following disclosure and accompanying drawings.

In accordance with the invention, generally stated, a radiopaque composition for use in cleaning and visualizing dental anatomy, patholigical conditions, and iatrogenic conditions in vivo in a living patient is provided. The composition can be used, for example to clean a root canal system of a tooth and to visualize the root canal systems using X-rays. The composition comprises a radiopaque iodine solution and a sodium hypochlorite solution. The iodine solution is made of diatrizoate meglumine and sodium iodine. The sodium hypochlorite solution is preferably a 1.5%–5% sodium hypochlorite solution. The iodine solution is preferably a 90% iodine solution and has substantially the same specific gravity as the sodium hypochlorite solution.

The iodine solution and sodium hypochlorite solution are mixed in a ratio of between 5:95 to 95:5, by volume. Preferably, the iodine solution and sodium hypochlorite solution are mixed in a ratio of between 30:70 to 70:30, by volume. And more preferably, the iodine solution and sodium hypochlorite solution are mixed in a ratio of between 45:55 to 55:45, by volume.

In use, the tooth to be treated is liberally flushed with the composition or mixture of the present invention such that the composition will substantially flow into the tooth anatomy or pathological condition to be visualized and treated. In visualizing a root canal system, the composition is flushed into the root canal system of a tooth once sufficient access to the pulp chamber has been made. The sodium hypochlorite portion of the composition will digest and remove pulp in the canal system and destroy and remove organisms and irritants within the root canal system. As the composition flows into the cleared out spaces of the canal system, the iodine portion of the composition will enable the dentist to take a high contrast X-ray which will enable him to visualize the anatomy of the root canal systems, monitor the preparation procedure, visualize pathological conditions, and visualize iatrogenic events.

DESCRIPTION OF THE PREFERRED EMBODIMENT

An endodontic procedure involves accessing the pulp chamber, identifying the orifice(s), cleaning and shaping the root canal systems, and then obturating the root canal systems. During the cleaning and shaping step, the root canal systems are liberally flushed with a solution, such as a 1.5%–5% solution of sodium hypochlorite (NaOCl). This is an anti-viral, anti-microbial, digestant, and oxidant. This solution will access all aspects of the root canal system to digest the remaining pulp and to eliminate any existing microbes, viruses, spores, and irritants, etc., which may be in the canal. At the same time, the sodium hypochlorite solution will bleach the outer surfaces of the tooth, to correct discoloration caused by the diseased pulp.

Once the root canal system is prepared for obturation, ideally, the canal system is visualized to confirm the completeness of the preparation of the root canal systems, monitor the remaining tooth structure, and guard against iatrogenic events. If pulp remains in the root canal space, further preparation of the root canal systems can be performed prior to obturation. My invention includes flushing the root canal systems with a new composition which is radiopaque or roetgenopaque and which has anti-microbial, pulp digesting, oxidizing, and bleaching characteristics. Such a substance is radiopaque and will show up as white (rather than as shadows) on an X-ray of the root canal system to enable the dentist to better visualize the root canal system, monitor the cleaning and preparation step, visualize other pathological conditions, and monitor the remaining tooth structure.

The composition preferably is a mixture of a radiopaque solution and sodium hypochlorite. The sodium hypochlorite is preferably a 1.5%–5% solution. One biocompatible radiopaque solution which may be used is available from Sterling-Winthrop, Inc. of New York, N.Y. under the name Hypaque®. Hypaque-M is a high concentration, highly viscous aqueous solution of two iodine salts, diatrizoate meglumine and sodium iodine. It has a pH of about 6.5–7.7 and is stable at room temperature. The Hypaque-M is preferably used as a 90% solution of Hypaque-M, which has approximately the same specific gravity as the sodium hypochlorite solution. The radiopaque solution is mixed with the sodium hypochlorite solution in a ratio of between 5:95 to 95:5, by volume. Preferably, the ratio of the radiopaque solution to the sodium hypochlorite is 30:70 to 70:30, and most preferably 45:55 to 55:45.

When using my composition, once the pulp chamber has been sufficiently accessed and the orifice(s) identified, the pulp chamber is flushed with the solution while the dentist probes the root of the canal systems. The composition or mixture of the present invention will digest the pulp in the canal system and destroy and remove any microbes, spores, etc. which may be in the canal system. Because the solution is radiopaque, the cleaning and shaping procedure can be monitored via X-rays to confirm the completeness of the preparation and cleaning procedure, and to determine the amount of remaining tooth material. That is, a different solution is not needed for the cleaning function and the visualizing function. The ability to monitor the preparation and shaping procedure will enable the dentist to avoid removing too much material (over preparing the canal system) which could lead to perforations or a weakening of the tooth structure. The radiopaque solution will be able to access the full extent of the root canal system, and will provide a high contrast X-ray to enable the dentist to better visualize the root canal system and the preparation.

As can be appreciated, although the invention is described with respect to visualizing the root canal system anatomy, the radiopaque solution can also be used to visualize other dental anomalies, such as pathological and iatrogenic conditions to aid the dentist in diagnosing and determining the treatment prognosis for a variety of pathological conditions, iatrogenic mishaps, and other clinically relevant factors. The solution may be used, for example, to assist in the diagnosis and extent of tooth fractures, distinguish between internal and external resorptions, and map the size and extent of resorptive perforations. The various anatomical and pathological conditions of the tooth are determined by flushing or injecting the tooth anatomy or pathology to be visualized with the solution and then X-raying the tooth. The use of the sodium hypochlorite is beneficial in these instances as well, to clean the anatomy and eliminate pathology by removing unwanted microbial organisms and irritants harbored within the anatomy of the root canal system.

As variations within the scope of the appended claims may be apparent to those skilled in the art, the foregoing description is set forth only for illustrative purposes and is not meant to be limiting. For example, other non-toxic, biocompatible radiopaque solutions or anti-microbial solutions can be used. This example is merely illustrative.

I claim:

1. A diagnostic composition for visualizing dental anatomy, pathology and iatrogenic events and removing pulp tissue and irritants, when present, from a tooth in vivo in a patient's mouth, the composition comprising a radiopaque solution and an anti-microbial cleaning solution, the anti-microbial cleaning solution being capable of digesting and removing pulp, microbial organisms, and irritants from a patient's tooth.

2. The composition of claim 1 wherein the radiopaque solution is an organic iodine solution and the cleaning solution is a sodium hypochlorite solution.

3. A diagnostic visualization composition for visualizing dental anatomy, pathology and iatrogenic events, the composition comprising a radiopaque solution and an anti-microbial cleaning solution, the anti-microbial cleaning solution being capable of destroying and removing pulp, microbial organisms, and irritants from a patient's tooth; said radiopaque solution being an organic iodine solution comprising diatrizoate meglumine and sodium iodine; the cleaning solution being a sodium hypochlorite solution.

4. The composition of claim 3 wherein the iodine solution and sodium hypochlorite solution are mixed in a ratio of between 5:95 to 95:5, by volume.

5. The composition of claim 4 wherein the iodine solution and sodium hypochlorite solution are mixed in a ratio of between 30:70 to 70:30, by volume.

6. The composition of claim 5 wherein the iodine solution and sodium hypochlorite solution are mixed in a ratio of between 45:55 to 55:45, by volume.

7. The composition of claim 3 wherein the composition is injectable.

8. The composition of claim 3 wherein the composition has a viscosity sufficiently low to enable the composition to wet substantially all of the surfaces desired to be visualized.

9. The composition of claim 8 wherein the iodine solution has a specific gravity no greater than approximately the specific gravity of the sodium hypochlorite solution.

10. A method for substantially simultaneously visualizing and cleaning dental anatomy, pathology, and iatrogenic events; the method including:

providing a mixture of a radiopaque solution and an anti-microbial solution capable of wetting the surfaces of the dental anatomy, anomaly, pathology, or iatrogenic event to be visualized and treated;

irrigating the dental anatomy, anomaly, pathology, or iatrogenic event to be visualized and cleaned with the mixture to wet the surfaces of the dental anatomy, anomaly, pathology, or iatrogenic event to be visualized and cleaned; and X-raying the tooth.

11. The method of claim 10 including a prior step of exposing the dental anatomy, anomaly, or pathology prior to irrigating the anomaly or pathology with the mixture.

12. The method of claim 11 wherein the dental anatomy, anomaly or pathology is the root canal system of a patient's tooth.

13. The method of claim 10 wherein the radiopaque solution is an organic iodine solution and the anti-microbial solution is a sodium hypochlorite solution.

14. The method of claim 13 wherein the iodine solution consists essentially of diatrizoate meglumine and sodium iodine.

15. The method of claim 14 wherein the iodine solution and sodium hypochlorite solution are mixed in a ratio of between 5:95 to 95:5, by volume.

16. A method for performing an endodontic procedure on a tooth in vivo in a living patient, the tooth having an enamel portion, dentine within the enamel, a root canal system comprising one or more root canals having pulp, bacteria, and related irritants therein; the method comprising:

exposing the root canal system;

removing the pulp from the root canal system;

flushing the root canal system with an anti-microbial solution which will digest pulp and destroy organisms in the canal system;

applying a radiopaque solution to the root canal system;

X-raying the root canal system to determine the configuration of the root canal system; and obturating the root canal system.

17. A method for performing an endodontic procedure on a tooth, the tooth having an enamel portion, dentine within the enamel, a root canal system comprising one or more root canals having pulp, bacteria, and related irritants therein; the method comprising:

exposing the root canal system;

removing the pulp from the root canal system;

flushing the root canal system with an anti-microbial solution which will digest pulp and destroy organisms in the canal system;

applying a radiopague solution to the root canal system;

X-raying the root canal system to determine the configuration of the root canal system; and obturating the root canal system;

wherein the steps of flushing the root canal system and applying a radiopaque solution to the root canal system are performed simultaneously.

18. The method of claim 17 wherein the flushing step includes flushing the tooth with a radiopaque anti-microbial solution.

19. The method of claim 18 wherein the radiopaque anti-microbial solution is a mixture of an organic iodine solution and a sodium hypochlorite solution.

20. The method of claim 19 wherein the organic iodine solution and sodium hypochlorite solution are mixed in a ratio of between 5:95 to 95:5, by volume.

21. The method of claim 20 wherein the iodine solution comprises diatrizoate meglumine and sodium iodine.

22. A radiopaque composition for use in preparing a root canal system of a tooth for an endodontic procedure in vivo in a living patient, including removing pulp tissue and irritants, when present, and for visualizing the anatomy, pathology, and iatrogenic conditions of the root canal system using X-rays, the composition consisting essentially of a radiopaque iodine solution and a sodium hypochlorite solution.

23. A radiopague composition for use in preparing a root canal system of a tooth for an endodontic procedure and for visualizing the anatomy, pathology, and iatrogenic conditions of the root canal system using X-rays the composition consisting essentially of a radiopague iodine solution and a sodium hypochlorite solution; the iodine solution and sodium hypochlorite solution being mixed in a ratio of between 5:95 to 95:5, by volume.

24. The method of claim 23 wherein the iodine solution comprises diatrizoate meglumine and sodium iodine.

* * * * *